Figure 1:
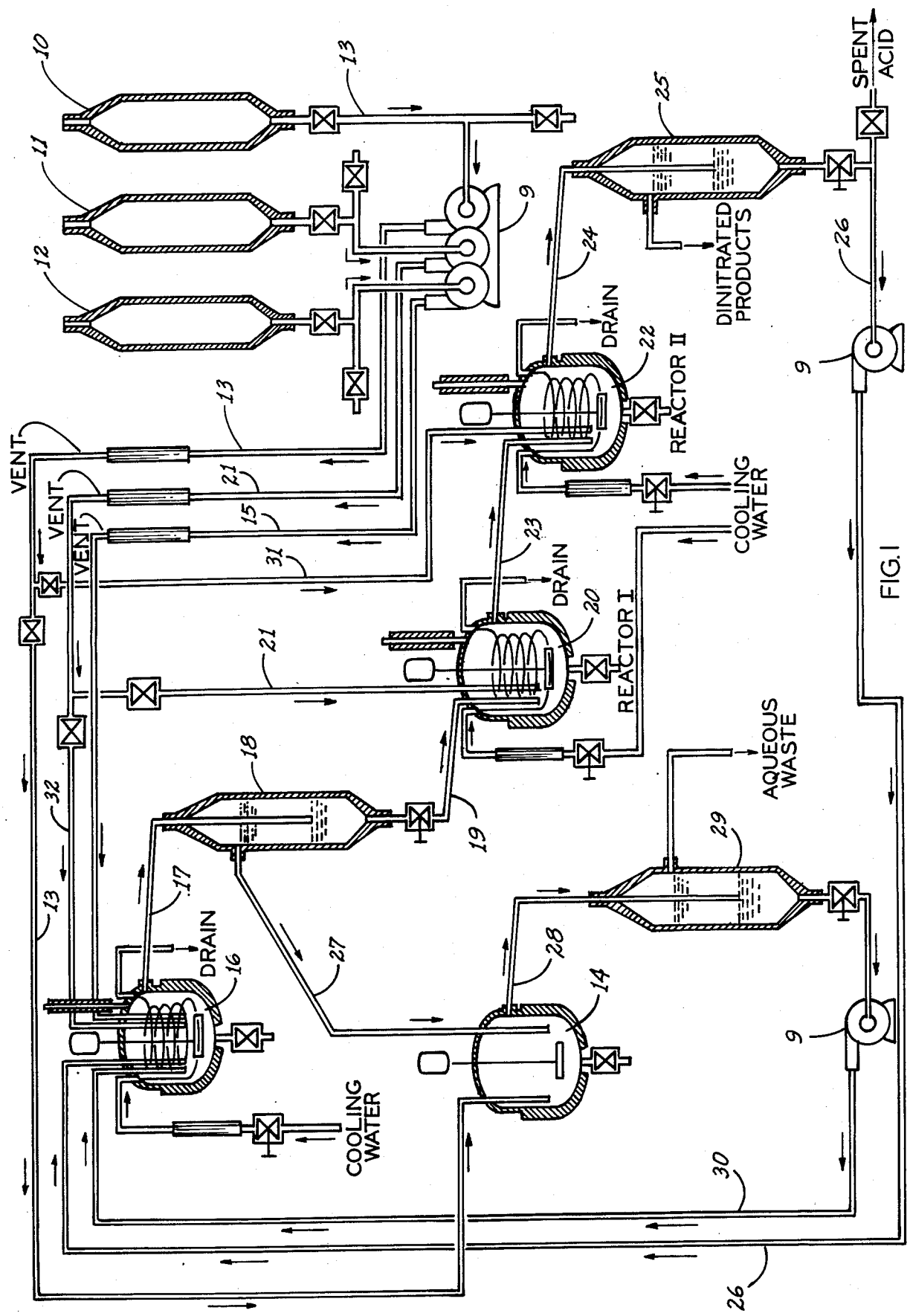

United States Patent [19]

McDaniel

[11] Patent Number: 4,621,157

[45] Date of Patent: Nov. 4, 1986

[54] NITRATION PROCESSES

[75] Inventor: Larry A. McDaniel, Germantown, Tenn.

[73] Assignee: Jerome A. Gross, St. Louis, Mo. ; a part interest

[21] Appl. No.: 607,794

[22] Filed: May 7, 1984

[51] Int. Cl.$^4$ ............... C07C 85/24; C07C 79/10
[52] U.S. Cl. ............... 564/411; 568/932; 568/933; 568/934; 568/940; 260/688
[58] Field of Search ............... 568/932–934, 568/939, 940, 630, 648, 655; 564/411; 71/121; 260/688

[56] References Cited

U.S. PATENT DOCUMENTS

| | | | |
|---|---|---|---|
| 2,739,174 | 3/1956 | Ross | 568/940 |
| 3,726,923 | 4/1973 | Foster et al. | 564/411 |
| 3,780,116 | 12/1973 | Sahgal | 260/688 |
| 3,836,601 | 9/1974 | Frey et al. | 260/688 |
| 3,927,127 | 12/1975 | Damiano | 568/933 |
| 4,036,838 | 7/1977 | Vogel et al. | 568/932 |
| 4,096,195 | 6/1978 | Schneider et al. | 568/933 |
| 4,112,005 | 9/1978 | Thiem et al. | 564/411 |
| 4,136,117 | 1/1979 | Diehl et al. | 71/121 |
| 4,165,231 | 8/1979 | Lutz et al. | 71/121 |
| 4,496,782 | 1/1985 | Carr | 568/932 |

OTHER PUBLICATIONS

Glazer et al., "Kinetics & Mechanism of Aromatic Nitration, Part VII, Products of Nitration of Aniline Derivatives, Especially of Dimethylaniline", Journal of Chemical Society, 1950, pt. 3, pp. 2657–2678.

Primary Examiner—John F. Terapane
Assistant Examiner—Anne Brookes
Attorney, Agent, or Firm—Jerome A. Gross

[57] ABSTRACT

The present invention relates to improvements in processes of preparing dinitrated aromatic compounds, particularly dinitrated aniline and dinitrated substituted aniline compounds, employing relatively dilute and then more concentrated nitric acid as the nitrating agent.

6 Claims, 1 Drawing Figure

NITRATION PROCESSES

TECHNICAL FIELD

The present invention relates to improvements in processes for preparing dinitrated aromatic compounds, particularly aromatic compounds such as aniline and substituted aniline compounds, employing relatively dilute and then more concentrated nitric acid as the nitrating agent. Moderate reaction temperatures are used. In these processes two nitro groups are introduced in the benzene or aromatic ring of the compound to be nitrated.

BACKGROUND ART

It has been common practice in the past in the preparation of dinitro aromatic compounds to use concentrated nitric acid containing sulfuric acid as a catalyst, as the nitrating medium. This is as exemplified, in U.S. Pat. No. 4,136,117 to Robert E. Diehl and Stephen D. Levy, issued Jan. 23, 1979. Also it is known from the same patent (col. 1, lines 52-60) that Belgium Pat. No. 762,232 discloses a method for the preparation of 2, 6-dinitro-tertiary anilines, wherein both N-substituents are haloalkyl, by nitration with at least a five fold excess of nitric acid, which is present at the start of the reaction in a concentration of 50% to 90% and in an amount to leave an acid concentration of 50% at the end of the reaction, in the presence of a catalytic amount of nitrous acid or nitrite ion generating material.

Each of the above processes have disadvantages from an economical and environmental standpoint. The processes utilizing mixtures of nitric acid and sulfuric acid generate spent acids containing 40% or more acid, including some nitric acid. This spent acid either has to be neutralized prior to disposal—resulting in the generation of considerable amounts of mixtures of sodium nitrate and sodium sulfate which must be disposed of in the environment—or the spent acid must be concentrated by evaporation of water (with expenditure of energy) to a concentration which can be used for subsequent nitration reactions.

In the other process, referred to above, in which a five fold excess of concentrated nitric acid is utilized along with a nitrous acid or nitrite ion generating material, the spent acid from the dinitration process contains 50% or more of nitric acid. This spent acid, like that containing sulfuric acid, must either be concentrated prior to use in the dinitration process or must be neutralized, for example, to form sodium nitrate, and then disposed of in the environment.

DISCLOSURE OF THE INVENTION

The present invention has, as one object, the elimination or minimizing of the above described disadvantages. In accordance with the present invention, the first nitro group is introduced into the aromatic compound, for example, aniline or phenol, by reacting such compound at moderate temperature and pressure conditions, for example, about 40°-65° C. and atmospheric pressure, with a relatively dilute aqueous nitric acid of the order of 10%-50% by weight $HNO_3$ concentration in the presence of a suitable liquid, water-immiscible organic solvent for the nitratable compound; for example, a solvent such as dichloroethane. In the case of aniline, the compound formed is either mononitroaniline or a reaction product of aniline and nitric acid which is believed to be a salt of aniline and nitric acid. In the case of phenol, the compound formed is mononitro phenol. The resulting mixture is then allowed to separate into an organic phase containing such solvent and the nitrated aromatic compound and a water phase which contains 10% by weight or less of $HNO_3$.

Next the nitratable aromatic compound in the organic phase is reacted with a relatively concentrated aqueous nitric acid of about 60%-100% by weight $HNO_3$ concentration at moderate temperature and pressure conditions, for example, of the order of 40°-70° C. and atmospheric pressure. In this reaction the aromatic compound is dinitrated, that is, two nitro groups are introduced into the aromatic ring of the compound. In the case of phenol, a dinitro phenol is formed and in the case of aniline, the reaction results in the formation of the dinitroaniline. The spent (more dilute) acid from this step can then be reacted with aniline as described in the first step above.

Although reference has been made above to the reaction of nitric acid and aniline, the processes of this invention are also applicable to the dinitration of nitratable aromatic compounds in general, and to substituted anilines, phenol and substituted phenols in particular, as will be described in greater detail hereafter.

The processes of this invention are carried out using nitric acid which is substantially free of sulfuric acid, but which may be free of or may contain catalytic amounts of nitrous acid or nitrite ion generating material. It is preferred to use pure or technical grade nitric acid as made and sold commercially as the nitrating agent in the second step, and free from additives or catalytic additives.

THE DRAWINGS

The accompanying drawing, FIG. 1, is a flow diagram which is a schematic representation of equipment which can be used to carry out one of the preferred embodiments of the processes of this invention involving the dinitration of substituted aniline compounds.

BEST MODE FOR CARRYING OUT THE INVENTION

In FIG. 1, numerals 10, 11 and 12 represent, respectively, storage tanks for the liquid organic solvent, liquid nitric acid, and the liquid substituted aniline compound to be dinitrated in the process. By means of one of the pumps 9, pipe line 13, connected to tank 10, conveys solvent from storage tank 10 to solvent extractor 14. Pipe line 15, connected to tank 12, similarly conveys the substituted aniline from storage tank 12 to the reactor 16, for reaction with a dilute or spent nitric acid from a source to be described below. The reaction mixture overflow from reactor 16 flows via pipe line 17 to a separator 18 in which the substituted aniline-nitric acid reaction product (also referred to as aniline salt) is separated from the aqueous phase of the reaction mixture as a lower layer which can flow via pipe 19 to a reaction vessel 20 (designated Reactor I). Concentrated nitric acid is conveyed to vessel 20 via pipe 21 from storage tank 11. Dinitration is carried out in vessel 20 and vessel 22 (designated Reactor II) which provide sufficient dwell time to insure that a dinitrated product is obtained; the reaction mixture in vessel 20 overflows from that vessel through pipe 23 to vessel 22 where additional dwell time is provided. The overflow from vessel 22 flows through pipe line 24 to separator 25 in which the dinitrated product is allowed to separate from the aqueous spent nitric acid. This spent acid is then pumped through pipe 26 to reactor 16 for reaction with additional substituted aniline.

The upper layer (aqueous phase) in separator 18 flows via pipe 27 to the solvent extractor 14 and the overflow from this extractor flows via pipe 28 to separator 29 wherein the solvent and aqueous phase are allowed to separate into an upper aqueous phase, which is waste, and a solvent lower phase which solvent phase is pumped via pipe line 30 to reactor 16.

There is also provided, in FIG. 1, pipe line 31 which is connected to organic solvent pipe line 13 and permits solvent to be pumped from storage tank 10 to reactor 22 (Reactor II), if required. In addition, pipe line 32 is provided to convey nitric acid, if required, from pipe line 21 (connected to storage vessel 11) to reactor 16.

As is indicated in FIG. 1 alll reaction vessels 16, 20 and 22 are provided with cooling coils and agitators to provide temperature control and intimate mixing of the vessel contents, and also with condensers to condense vapors back into the reactors. Conventional valves are used as shown in the drawing.

As noted above, the present invention is practiced in several steps, one of which comprises reacting a dinitratable aromatic compound, for example, aniline or a substituted aniline, with an aqueous dilute or spent nitric acid (from another step as described hereinafter) of about 20%–50% by weight HNO'hd 3 in the presence of a suitable liquid, water-immiscible organic solvent. In most instances the mole ratio of nitric acid to aromatic compound is about 1:1 to about 1.8:1, preferably about 1:1 to about 1.5:1. This step is generally carried out at atmospheric pressure of the order of about 700–790 millimeters of mercury and at moderate temperatures of the order of 40°–70° C. These temperatures are maintained by cooling the reactants, if necessary. Generally cooling is necessary.

In the following description the term "an aniline'38 is intended to include aniline or a substituted aniline, and the substituted aniline can be N-substituted, that is, have one or two substituent groups instead of hydrogen or the nitrogen atom or can be ring substituted, or both.

Any dinitratable aromatic compound can be used in the present process. A particularly suitable class of dinitratable aromatic compounds which can be used are aniline, and substituted anilines of the following Formula I:

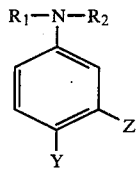

I wherein:
Y is hydrogen, halogen, alkyl $C_1$–$C_4$, alkenyl $C_2$–$C_4$, —CN, —$SO_2NR_3R_4$ or $CF_3$;
Z is hydrogen, alkyl $C_1$–$C_4$, alkenyl $C_2$–$C_4$, or mono-substituted alkyl $C_1$–$C_4$ where the substituent can be halogen, alkoxy $C_1$–$C_4$ or —N—$R_3R_4$;
$R_1$ is hydrogen, alkyl $C_1$–$C_6$, alkenyl $C_2$–$C_6$ or alkynyl $C_2$–$C_6$;
$R_2$ is aklyl $C_2$–$C_7$ (straight, branched or cyclo), alkenyl $C_214$ $C_6$, alkynyl $C_2$–$C_6$, or mono-substituted alkyl $C_1$–$C_4$ where the substituent is halogen or alkoxy $C_1$–$C_4$;

$R_3$ and $R_4$ each are hydrogen or alkyl $C_1$–$C_4$ and when $R_1$ and $R_2$ are taken together they represent piperidino, pyrolidino or morpholino.

Illustrative of substituents falling within the above definition are those described in U.S. Pat. No. 4,165,231 (column 1, lines 53–65) issued on Aug. 21, 1979, to Albert W. Lutz and Robert F. Piehl, which description is hereby incorporated herein by reference. Illustrative of compounds falling within the above Formula I are the non-nitrated compounds described in columns 3 and 4 of the same patent, that is, the compounds described in these columns but which have no nitro substituents. Such compounds are hereby incorporated herein by reference.

Preferred substituted aniline compounds for dinitration within the scope of Formula I are those of the following Formula II:

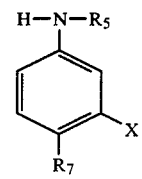

II wherein,
$R_7$ is $CH_3$, $C_2H_5$, $C_3H_7$—n, $C_3H_7$—i, $C_4H_9$—i, $CF_3$ or Cl,
X is $CH_3$, $CH_2$—O—$CH_3$ or —$CH(CH_3)OCH_3$; and
$R_5$ is $C_3$–$C_7$ secondary alkyl, or monochloralkyl $C_3$–$C_4$.

The 2, 6 dinitro derivatives of the substituted aniline compounds within the scope of Formula II are stated to be preemergence herbicides in the above U.S. Pat. No. 4,165,231, except for the exclusions referred to in said patent.

The preferred substituted aniline compounds to be dinitrated in accordance with the present invention are N-sec-butyl-3, 4-xylidine, N-(1-ethylpropyl)-3, 4-xylidine and N-(1-methylbutyl)-3, 4-xylidine.

Another suitable class of aromatic compounds which can be dinitrated in accordance with the present invention are phenol or substituted phenols of Formula III below:

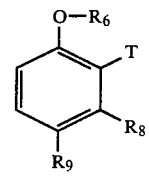

III wherein
$R_6$ is hydrogen, alkyl $C_1$–$C_{12}$, alkoxy $C_2$–$C_6$, halosubstituted alkyl $C_1$–$C_{12}$, or alkylalkoxy $C_3$–$C_8$;
$R_9$ is alkyl $C_1$–$C_6$, alkoxy $C_2$–$C_6$, halosubstituted aklyl $C_1$–$C_6$, hydrogen, halogen, amino or substituted amino;
$R_8$ comprises the same substituents as U; and
T comprises the same constituents as U and V with the further proviso that if both U and V are other than hydrogen then T is hydrogen.

Illustrative alkyl substituents when alkyl is $C_1$–$C_6$ are methyl, ethyl, n-propyl, iso-propyl, n-butyl, t-butyl, pentyl, sec. butyl, 2-pentyl and the like, and when alkyl is $C_1$–$C_{12}$ the foregoing substituents plus n-octyl 2-octyl, 6-octyl, 2-propylhexyl, decyl, dodecyl and the like.

Illustrative of $C_1$–$C_6$ alkenyl substituents are ethenyl, 1-propenyl, 2-propenyl, 1-butenyl, 2-butenyl, 1-pentenyl, 2-hexenyl and the like.

The preferred phenols for use in the dinitration processes of the present invention are phenol, o-cresol, o-secbutyl phenol, octyl phenol, decyl phenol and dodecyl phenol, and these compounds fall within the scope of Formula III when U and V are hydrogen and $R_6$ is one of the above named substituent groups or in the case of o-cresol, T is methyl and U, V and $R_6$ are hydrogen.

As previously noted above, when an aniline is reacted with the spent nitric acid, the reaction product can be a mononitrated product or the reaction product of an aniline and nitric acid, which for convenience is sometimes referred to herein as an aniline salt. Whether the reaction product is mononitrated or such salt will depend on the particular substituted aniline compound used, the concentration of the spent nitric acid employed and the mole ratio of $HNO_3$ to aniline compound. In general, if the aniline compound used falls within the scope of Formula I or II and the concentration of the spent nitric acid is about 10%–40% by weight of $HNO_3$ and the mole ratio is about 1:1 to about 1.3:1, an aniline salt is formed. With such spent acid concentration and compounds within the scope of Formula I, in most instances an aniline salt will be formed. With higher spent acid concentrations, the reaction product will usually be the mononitro derivative of the aniline or substituted aniline compound. This is usually also the case if the spent acid concentration is about 35% and the $HNO_3$ to aniline mole ratio is above 1.3:1.

There is a considerable advantage in forming an aniline salt in that the subsequent reaction thereof with concentrated nitric acid to form the dinitro derivative proceeds quickly and smoothly, and with the formation of a spent nitric acid concentration for use in reaction with additional substituted aniline. Moreover, the generation of a spent acid which can be used for an aniline salt formation results in a nitric acid recycle operation in which comparatively very little nitric acid must be neutralized, concentrated or discarded, in contrast to prior practice. The spent nitric acid concentration required to form an aniline salt can be quite low, for example, 10% by weight $HNO_3$, and when such salt forms it is quite soluble in the organic solvent used and separates essentially completely from the aqueous phase containing any residual nitric acid which can be 1% by weight $HNO_3$ or lower. This is the only nitric acid waste generated in the process. The resulting aniline salt is then dinitrated as described below.

There also are thermodynamic advantages in the processes of this invention in which an aniline is to be dinitrated and an aniline salt is formed using spent nitric acid of the concentrations herein described, as compared to a standard straightforward nitration. In the latter type of nitration, either batch or continuous, an aniline is mixed with the concentrated nitrating acid to form the dinitro aniline and water, with a heat of reaction of the order of $-30$ Kcal/gram mole for each $NO_2$ group added. During the reaction, all of this heat must be removed by cooling, with the exception of the heat used to raise the temperature of the reactants to reaction temperature.

In contrast, when an amine salt is formed first and then reacted with concentrated nitric acid to form the dinitrated product, as in the present process, there is a division of reactions and therefore a division of heats. Thus, when an aniline in a solvent is reacted with spent or dilute nitric acid of about 20%–25% by weight $HNO_3$ concentration, the heat of aniline salt formation is just about enough to raise the temperature of the reaction mixture to about 60° C. or the desired temperature. Consequently no heating or cooling are required. When the aniline salt in the solvent is then reacted with more concentrated $HNO_3$, the heat of dinitration is approximately the same as in the standard straightforward dinitration but in contrast thereto, another reaction must take place, namely, aniline salt dissociation. This dissociation is the reverse reaction of the salt formation and therefore is endothermic, taking up about as much heat as the salt formation process gives off. This is true whether the salt dissociation takes place before, as is probably the case, or after the dinitration reaction. It can be seen from the foregoing that, in the aniline salt formation process and dinitro group introduction into the aniline compound, the heat of formation or reaction of about one $NO_2$ group is eliminated in contrast to the standard dinitration, and this results in the elimination of a very high heat load in the first stage reactor of the dinitration process. Stated differently, only half the usual cooling is required, thus saving energy, and the danger of hot or runaway nitration reactions is substantially reduced.

When phenol or substituted phenols are nitrated in accordance with the present invention, the reaction product with the spent nitric acid (about 34%–50% $HNO_3$ by weight) is a mononitrophenol, primarily 2-nitrophenol and 4-nitrophenol, or 2-nitro substituted phenol or 4-nitro substituted phenol. There is no phenol nitric acid salt formation, as in the case of substituted anilines as described above, unless the phenol contains amino or substituted amino groups on the benzene ring.

In practicing another or second step of the present process, the mononitro derivative of the aromatic compound, such as phenol or an aniline salt, prepared as described in the above discussion and dissolved in the organic solvent phase of the first step, is reacted with a more concentrated aqueous nitric acid. As noted previously herein, the nitric acid concentration is about 60%–100% by weight of $HNO_3$, and is preferably 65%–75% by weight of $HNO_3$. This reaction is carried out at moderate temperature and pressure conditions, that is, temperatures of about 40°–70° C., preferably 50°–65° C., and pressures of the order of 700–790 millimeters of mercury. These pressures correspond essentially to prevailing or ambient atmospheric pressures.

In carrying out this dinitration (second) step, the mole ratio of the more concentrated $HNO_3$ to aniline compound can vary to some extent but is desirably 1.9:1 to 2.5:1, and preferably about 2.0:1 to about 2.3:1, to obtain the advantages of the present invention in reusing the resulting spent nitric acid in the first step of the process, that is, mononitration or aniline salt formation.

As noted above, both nitration steps are carried out in the presence of a suitable liquid, water-immiscible organic solvent for the aromatic compound which is being nitrated. A large variety of liquid, water-immiscible solvents can be used but such solvents should be substantially less reactive to nitric acid than the compound which is to be dinitrated and are, preferably, inert to or non-nitratable by nitric acid under the reaction conditions described herein. The relative ease of nitration of various compounds has been described in the literature. By way of illustration, the following is the declining order of reactivity of some compounds with nitric acid: aniline, phenol, mesitylene, xylene, monochlorobenzene (MCB). It is thus possible to use xylene or MCB as the solvent in the reaction if aniline or phenol are being nitrated. A particularly suitable class of solvents which can be used and which are inert to nitration under the herein described reaction conditions are liquid chloro or chloro and fluro derivatives of saturated alkanes (straight chain or branched), preferably of 1 to 6 carbon atoms. Specific examples of this class of solvents are dichloroethane, trichlorethane, carbon tetrachloride, chloroform and the like. Dichlorethane is the solvent of choice. The amount of such organic solvent used should be sufficient to maintain the aromatic compound and its various nitrated derivatives formed in the process in solution in such solvent.

The reaction with more concentrated nitric acid to produce the dinitro derivative of the aromatic compound is allowed to proceed to completion, that is, until two nitro groups are introduced into the aromatic ring of such compound. When the aromatic compound used is aniline or a mono-N-substituted aniline, with no ring substitution, the primary reaction product formed is the 2, 4-dinitro derivative, that is, 2, 4-dinitro aniline or the 2, 4-dinitro mono-N-substituted aniline. There will also be formed relatively small amounts of the N-nitroso derivative of such dinitro compounds. When the aromatic compound used is a di-N-substituted aniline, for example, dimethylaniline, the primary reaction product is also the 2, 4-dinitro derivative, but in the case of such an aniline no nitroso derivative is formed. When the substituted aniline has substitutent groups in the 3, 4 position, on the benzene ring, for example, the dinitro reaction product will be primarily a 2, 6-dinitro derivative.

By way of illustration, if the aromatic compound to be dinitrated is a mono-N-alkyl substituted 3, 4-alkyl substituted aniline, the reaction product is primarily the 2, 6-dinitro derivative and small amounts of the N-nitroso derivative. Such derivative can be converted to additional 2, 6-dinitro derivative, as will be described in greater detail hereafter.

When the starting aromatic compound is phenol or substituted phenol, with a substituent group on the oxygen atom, the final reaction product, after dinitration, is primarily 2, 4-dinitro phenol or 2, 4-dinitro substituted phenol.

The present invention is further illustrated by the following specific examples which are intended to be illustrative, but not limitative, parts and percentages being by weight unless otherwise specified.

EXAMPLE 1

In the first step, a solution containing 576 grams of dichloroethane and 368 grams of 95% N-(1-ethylpropyl)-3, 4-dimethyl aniline (1.83 mole) was mixed with 328 grams (1.83 mole) of spent aqueous nitric acid of 35.1% $HNO_3$ concentration at 60° C. for about 30 seconds. The spent acid used was obtained in the manner described in the second step of this Example. The mixture was allowed to separate into two (2) phases, that is, an organic phase and an aqueous phase. The organic phase (almost 1,100 grams) contained approximately 576 grams of dichlorethane, 349 grams of N-(1-ethylpropyl)-3, 4-dimethylaniline combined with 115 grams of $HNO_3$ (the combination is referred to as aniline salt) and 38 grams $H_2O$. The aqueous phase, of about 175 grams, contained less than 1% $HNO_3$ and less than 1% of the aniline compound.

In the second step, the organic phase from the first step was mixed with 362 grams (4.02 moles) of aqueous 70% $HNO_3$ at 60° C. The reaction mixture was stirred for one hour and maintained at 60° C. during that period, after which the mixture was allowed to separate into an organic phase and an aqueous phase consisting essentially of 328 grams (1.83 mole) of spent aqueous nitric acid (35.1% $HNO_3$), essentially the same as used in the first step of this Example. The organic phase contained N-(1-ethylpropyl)-3, 4-dimethyl-2, 6-dinitro aniline and N-nitroso-N-(1-ethylpropyl)-3, 4-dimethyl-2, 6-dinitro aniline. This phase was treated with 27 grams of 32% Hcl and 23.3 grams of sulfamic acid at 100° C. for three hours with occasional venting to maintain the pressure at 15–20 psi. The mixture was allowed to cool to 50° C., during which phase separation occurred. The aqueous phase was discarded and the organic phase was neutralized with 2% NaOH solution. The aqueous phase was separated and the dichlorethane was stripped off under vacuum. This resulted in denitrosation of the N-nitroso compound and additional yield of the desired N-(1-ethylpropyl)-3, 4-dimethyl-2, 6-dinitro aniline.

The spent acid of the second step can be used in another first step reaction.

EXAMPLE 2

In this Example, a reaction similar to that in Example 1 was carried out except the spent acid was of higher concentration and mononitration of the aniline compound was effected in the first step rather than aniline salt formation.

In the first step a solution of 368 grams (1.83 mole) of N-(1-ethylpropyl)-3, 4-dimethylaniline in 552 grams of dichlorethane was mixed with 343 grams of spent aqueous nitric acid of 51.3% $HNO_3$ concentration (2.79 moles) at 60° C. and stirred for one hour. The spent acid used was obtained in the manner described in the second step of this Example. The mixture was allowed to separate into two phases, that is, an aqueous phase and an organic phase, the latter yielding a total of about 987 grams containing approximately 437 grams of the mononitro derivative of the above mentioned aniline compound and 552 grams of dichloroethane. The aqueous phase consisted of about 253 grams of 20% $HNO_3$ concentration.

In the second step, the organic phase from the first step was mixed with 434 grams of aqueous nitric acid of 70% $HNO_3$ concentration (4.82 moles) at 60° C. and the mixture was stirred for one hour while maintaining the temperature of the mixture at 60° C. by cooling. The mixture was then allowed to separate into an organic phase and an aqueous phase which consisted of about 343 grams of spent aqueous nitric acid of 51.3% $HNO_3$ concentration, essentially the same as used, and usable, in the first step of this Example. This spent acid can be used per se in another first step reaction. The organic phase weighing about 1068 grams was composed primarily of N-(1-ethylpropyl)-3, 4-dimethyl-2, 6-dinitro aniline and minor amounts of N-nitroso-N-(1-ethylpropyl)-3, 4-dimethyl-2, 6-dinitro aniline. This phase was treated with hydrochloric acid and sulfamic acid in the same manner as described in the last paragraph of Example 1 to effect denitrosation of the N-nitroso compound in the organic phase and thus enhance the yield of desired product N-(1-ethylpropyl)-3, 4-dimethyl-2, 6-dinitro aniline.

EXAMPLE 3

The process described in Example 1 was repeated except 172 grams of aniline (1.83 moles) were used as the starting nitratable material instead of N-(1-ethylpropyl)-3, 4-dimethylaniline.

The organic phase obtained in the second step of the process contained essentially 2, 4-dinitro aniline and N-nitroso-2, 4-dinitro aniline. The aqueous spent nitric acid, obtained in the second step, had a 35% $NHO_3$ concentration. The organic phase was treated with hydrochloric acid and sulfamic acid in the manner described in the last paragraph of Example 1 to effect denitrosation of the N-nitroso compound and thus enhance the yield of the desired 2, 4-dinitro aniline.

EXAMPLE 4

This Example pertains to the dinitration of phenol. In the first step a solution of 172 grams of phenol (1.83 moles) and 576 grams of dichlorethane were mixed with 343 grams of spent aqueous nitric acid of 51.3% $HNO_3$ concentration (2.79 moles) at 60° C. and stirred for one hour. The spent acid used was obtained in the manner described in the second step of this Example. The mixture was allowed to separate into two phases, that is, an aqueous phase and an organic phase, the latter containing primarily a mixture of 2-nitro-phenol and 4-nitro-phenol in 576 grams of dichloroethane. The aqueous phase consisted of about 253 grams of aqueous spent nitric acid of 20% $HNO_3$ concentration.

In the second step, the organic phase from the first step was mixed with 434 grams of aqueous nitric acid of 70% $HNO_3$ concentration (4.82 moles) at 60° C. and the mixture was stirred for one hour while maintaining the temperature of the mixture at 60° C. by cooling. The mixture was then allowed to separate into an organic phase and an aqueous phase which consisted of about 343 grams of spent aqueous nitric acid of 51.3% $HNO_3$ concentration, essentially the same as used in the first step of this Example. This spent acid can be used per se in another first step reaction. The organic phase contained essentially all of the dichloroethane employed and dinitrophenol, primarily 2, 4-dinitrophenol.

EXAMPLE 5

The process of Example 4 was repeated except that 197 grams of o-creosol (1.83 moles) was used as the dinitratable aromatic compound instead of phenol. The aqueous phase obtained on phase separation after completion of the second step (dinitration step) contained about 340 grams of spent aqueous nitric acid of 51.5% $HNO_3$ concentration, essentially the same as used in the first step of this Example. This spent acid can be used per se in another first step reaction. The organic phase obtained on phase separation contained essentially all of the dichloroethane employed and dinitro o-creosol.

EXAMPLE 6

In the first step, a solution containing 576 grams of dichloroethane and 368 grams of 95% N-(1-ethylpropyl)-3, 4-dimethylaniline (1.83 moles) was mixed with 574 grams (1.83 moles) of spent aqueous nitric acid of 20% $HNO_3$ concentration at 60° C. for 30 minutes. The spent acid used was obtained in the manner described in the second step of this Example. The mixture was allowed to separate into two phases, that is, a lower organic phase and an upper aqueous phase. This phase separation was very clean and sharp, and the two layers were easily separated. The lower organic phase (almost 1,100 grams) contained approximately 576 grams of dichloroethane, 349 grams of N-(1-ethylpropyl)-3, 4-dimethylaniline combined with 114 grams of $HNO_3$, the combination being referred to as an aniline salt, and the balance being a small amount of $H_2O$. The aqueous phase of about 422 grams consisted of water and less than 1% $HNO_3$ and less than 1% of the starting substituted aniline compound.

In the second step, the organic phase from the first step was mixed with 362 grams (4.02 moles) of aqueous 70% $HNO_3$ concentration at 60° C. The reaction mixture was stirred for one hour and maintained at 60° C. during that period. Water was then added to the resulting mixture, which separated into a lower organic phase and an upper aqueous (spent nitric acid) phase containing 20% $HNO_3$ concentration. Because of this phase inversion, the dinitrated product would be removed at the base of vessel 25 and the spent acid removed as overflow, instead of as illustrated in FIG. 1. This spent acid also could be used as the nitrating agent in the first step of the process of this Example. The addition of water, as above, also results in a quenching of the dinitration reaction. The organic (lower) phase contained N-(1-ethylpropyl)-3, 4-dimethyl-2, 6-dinitro aniline and N-nitroso-N-(1-ethylpropyl)-3, 4-dimethyl-2, 6-dinitro aniline. This phase was treated with hydrochloric acid and sulfamic acid in the manner described in the last paragraph of Example 1 to effect denitrosation of the N-nitroso compound and thus enhance the yield of the desired N-(1-ethylpropyl)-3, 4-dimethyl-2, 6-dinitro aniline.

This Example illustrates the distinct advantages in using spent aqueous nitric acid of 20% or less $HNO_3$ concentration in the first step of the process, in that the aniline salt formed is quite soluble in the dichloroethane organic solvent which enables a sharp separation of the aqueous phase, which is essentially free of nitric acid, from the organic phase. the dinitration of this aniline compound in the organic phase in the second step with the more concentrated nitric acid then enables the formation of spent aqueous nitric acid of 35% $HNO_3$ concentration which can, as heretofore described, be used in a first step reaction with additional aniline compound and thus provides a continuous recycle procedure. This means that very little nitric acid need be discarded or concentrated in the entire process.

Further in regard to Example 6, the dilution of the mixture in the second step of the process therein and prior to phase separation, not only quenches the reaction, as is mentioned, but also lowers the density of the spent acid to a point below that of the dinitrated product-solvent phase, thereby causing the spent acid phase to separate to the top and the organic phase to the bottom. In addition, the solubility of the organic (solvent and dinitro product) constituents of the organic phase in the spent acid phase, is significantly lowered thus reducing carry over of these constituents into the spent acid phase.

EXAMPLE 7

The description in this Example is in reference to FIG. 1. Reactor 16 at atmospheric pressure (750 mm of mercury) was supplied with 202 grams of dichloroethane, 175 grams of N-(1-ethylpropyl)-3, 4-dimethylaniline (hereinafter in this Example referred to as substituted aniline, for convenience) and 164 grams of spent aqueous nitric acid of 35% of HNO$_3$ concentration, and the contents were maintained at 60° C. To the separator 18 at atmospheric pressure was added a mixture of 29 grams of such substituted aniline, 44 grams of dichloroethane and 30.28 grams of the same spent aqueous nitric acid, all of which were maintained at 60° C. To both solvent extractor 14 and separator 29 were added 570 grams of dichloroethane and 180 grams of water containing 1% HNO$_3$. To each of the reactors 20 (Reactor I) and 22 (Reactor II) were added 495 grams of a solution which was 40% N-(1-ethylpropyl)-3, 4-dimethyl-2, 6-dinitro aniline and 8% N-nitroso-N-(1-ethylpropyl)-3, 4-dimethyl-2, 6-dinitro aniline in dichloroethane to which was added, in each reactor, 238 grams of spent aqueous nitric acid of 35% HNO$_3$. The contents of these reactors were maintained at 60° C. All of the above is simply a way of starting up the continuous process, and the reactors and other equipment used were thus filled.

The continuous process was now operated by supplying 6.13 grams/minute of the substituted aniline, 9.2 grams/minute of dichloroethane and 5.47 grams/minute of spent aqueous 35% HNO$_3$ to reactor 16; and 6.04 grams/minute of aqueous 70% HNO$_3$ to reactor 20. This resulted in an overflow of emulsion from reactor 16 through pipe line 17 to separator 18, where the emulsion separated into an upper aqueous layer and a lower organic layer containing the substituted aniline compound-nitric acid salt and the solvent, which flowed through pipe 19 to reactor 20 to which the concentrated nitric acid was being supplied with agitation. The overflow from reactor 20 then flowed to reactor 22 through pipe 23. The overflow from reactor 22 then flowed to separator 25 through pipe 24. This overflow was an aqueous organic mixture which separated in separator 25 into a lower phase of aqueous nitric acid of about 35% HNO$_3$ which was pumped to reactor 16 at the flow rate referred to above (5.47 grams/minute), and an upper organic phase. This upper phase contained the desired product, namely, N-(1-ethylpropyl)-3, 4-dimethyl-2, 6-dinitro aniline, along with N-nitroso-N-(1-ethylpropyl)-3, 4-dimethyl-2, 6-dinitro aniline, and was continuously withdrawn from separator 25 and treated as hereafter described.

While the foregoing was occurring, the aqueous phase overflow from separator 18 was being conveyed to solvent extractor 14 via pipe 27 and concurrently there was being supplied to the extractor 14, 9.2 grams/minute of dichloroethane. The contents of extractor 14 were continuously stirred and the overflow from the extractor was conveyed to separator 29 where the overflow liquid was allowed to separate into an aqueous phase containing about 1% HNO$_3$ and a lower dichloroethane phase containing a low concentration of the substituted aniline. This lower (dichloroethane) phase was pumped back into reactor 16 to supply the dichloroethane to that reactor, as referred to above, at the rate of 9.2 grams/minute.

The above process was operated continuously for a 240 minute equilibration period maintaining the above flow rates and maintaining the reactor contents at a temperature of 60° C.±1° C. The volume of the system was such that 240 minutes equals about four residence times using the above flow rates. Then a collection period of 60 minutes of continuous operation was completed during which time the actual total raw material feeds were:

367.8 grams (1.83 moles) of N-(1-ethylpropyl)-3, 4-dimethylaniline;

362.4 grams (4.03 moles) of concentrated aqueous 70% HNO$_3$;

552 grams of dichloroethane;

328.2 grams (1,83 moles) of spent aqueous 35% HNO$_3$.

The product (organic phase) obtained from separator 25 during the 60 minute collection period consisted of 1,068 grams of solution containing 438 grams (1.5 moles) of N-(1-ethylpropyl)-3, 4-dimethyl-2, 6-dinitro aniline and 78.4 grams (0.24 mole) of N-nitroso-N-(1-ethylpropyl)-3, 4-dimethyl-2, 6-dinitro aniline along with dichloroethane. The total yield of the desired aniline was 95%. There was collected from the lower aqueous layer in separator 25 333 grams of spent aqueous nitric acid of 35% HNO$_3$ concentration, and from the upper aqueous layer in separator 29 there was collected 175 grams of aqueous waste of about 1% HNO$_3$ concentration. Denitrosation of the N-nitroso compound in the organic layer product from separator 25 was effected in the manner described in the last paragraph of Example 1 to give a yield of the desired product N-(1-ethylpropyl)-3, 4-dimethyl-2, 6-dinitro aniline of 533.7 grams.

It is apparent from this Example that the present process can be operated continuously to produce a dinitrated product in high yields, and with the generation of very low concentrations of nitric acid waste which can be disposed of cheaply and readily.

It will be noted from Example 7 that the continuous processes of this invention can be carried out in the following manner. A dinitratable aromatic compound dissolved in an inert organic solvent and dilute aqueous nitric acid of 20%-50% HNO$_3$ concentration are continuously supplied to a reaction zone with agitation and temperature control, as previously described above, and in a mole ratio of about 1:1 to about 1:1.5 of aromatic compound to HNO$_3$. The overflow from such zone is then conveyed continuously to a separation zone to allow the reaction mixture to separate into an organic phase and an aqueous phase. The organic phase, which contains the organic solvent and reaction product of the aromatic compound and nitric acid, is then supplied continuously to another reaction zone along with concentrated aqueous nitric acid of about 65% to about 80% by weight of HNO$_3$, with agitation and temperature control, as previously described above, with sufficient residence time to complete dinitration of the aromatic compound. In this step, the mole ratio of compound to acid suitable for batch operation, as described above, is employed in the continuous operation. The reaction mixture from this reaction zone is continuously supplied to the separation zone where the reaction mixture is allowed to separate into an organic phase containing the desired dinitrated aromatic compound and the organic solvent and an aqueous phase of spent nitric acid containing about 20%-50% by weight HNO$_3$. This aqueous phase is continuously returned to the first reaction zone for reaction with additional dinitratable aromatic compound. The organic phase is continuously removed from the separation zone and the organic solvent can be stripped from the desired dinitrated product by vacuum distillation, if desired.

The denitrosation step described in the last paragraph of Example 1, and as referred to in Examples 2, 3, 6 and 7, can be carried out under different and varied conditions as described in the aforementioned U.S. Pat. No. 4,136,117, column 3, lines 47-67; column 4, lines 1-13; column 7, Example 16; and column 8, lines 1-23 and Examples 17-24, the subject matter of which is hereby incorporated herein by reference.

In the dinitration of anilines, the spent acid resulting from the dinitration step is normally about 35%-40% or from 10%-50% $HNO_3$. In the processing of phenols, the spent acid from the dinitration may be as great as 50% $HNO_3$. To use these acids in the first step of the processes described, they may be substantially diluted, say to 10% concentration.

INDUSTRIAL APPLICABILITY

The present process has wide applicability to commercial processes for preparation of dinitrated aromatic compounds, including agricultural herbicides.

I claim:

1. A continuous process of dinitrating a dinitratable substituted aniline compound which comprises continuously supplying (1) an aqueous nitric acid of about 10-40% $HNO_3$ by weight and substantially free of sulfuric acid; (2) a substituted aniline compound and (3) a liquid, inert, water-immiscible organic solvent for said aniline compound, in a mole ratio of about 1:1 to about 1:1.3 $HNO_3$ to said aniline compound, to a reaction zone at a temperature of about 40° to about 70° C. and atmospheric pressure, thereby forming in said zone an emulsion containing a salt of said nitric acid and aniline compound, continuously conveying the overflow emulsion from said zone to a separation zone to allow continuous separation of said emulsion into an aqueous phase and an organic phase containing said salt and solvent, continuously conveying said organic phase to a second and third reaction zone and reacting said salt in the organic phase in said zones with an aqueous nitric acid of 65%-80% by weight $HNO_3$ and substantially free of sulfuric acid at a temperature of about 40° C. to about 70° C. at atmospheric pressure, in a mole ratio of $HNO_3$ to salt of about 1.9:1 to about 2.5:1, until the dinitro derivative of said aniline compound is formed and continuously removing said derivative in said organic solvent from the third reaction zone, said substituted aniline compound having the structural formula:

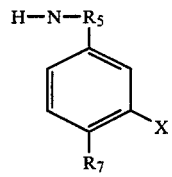

wherein:
$R_7$ is $CH_3$, $C_2H_5$, $C_3H_7$—n, $C_3H_7$—i, $C_4H_9$13 i, $CF_3$ or Cl;
X is $CH_3$, —$CH_2$—O—$CH_3$ or —$CH(CH_3)O$—$CH_3$; and
$R_5$ is $C_3$-$C_7$ secondary alkyl, or monochloralkyl $C_3$-$C_4$.

2. A process according to claim 1, wherein said aniline compound is n-sec. butyl-3, 4-xylidine, N-(1-ethylpropyl)-3, 4-xylidine or N-(1-methylbutyl)-3, 4-xylidine.

3. The continuous process defined in claim 1, wherein, in the step in which the said dinitro derivative is formed, a spent nitric acid is yielded in a concentration of about 10%-50% $HNO_3$ by weight, characterized in that the said spent acid so yielded is thereafter used in the first defined supplying step of said continuous process.

4. A process of dinitrating a dinitratable substituted aniline compound which comprises reacting (1) an aqueous nitric acid of about 10-40% $HNO_3$ by weight and substantially free of sulphuric acid with (2) a substituted aniline compound in the presence of a liquid, inert, water-immiscible organic solvent for said aniline compound, in a mole ratio of about 1:1 to about 1:1.3 of $HNO_3$ to said aniline compound and at a temperature of about 40° to about 70° C. and atmospheric pressure, thereby forming an emulsion containing a salt of said nitric acid and aniline compound dissolved in said solvent, separating said emulsion into an aqueous phase and an organic phase containing said salt, separating the organic phase from the aqueous phase and reacting said salt in the organic phase with an aqueous nitric acid of 65-80% by weight $HNO_3$ and substantially free of sulphuric acid in a mole ratio of $HNO_3$ to said salt of about 1.9:1 to about 2.5:1 and at a temperature of about 40° C. to about 70° C. and at atmospheric pressures until a reactive mixture containing the dinitro derivative of said compound is formed, said substituted aniline compound having the structural formula:

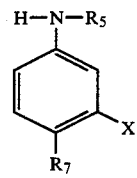

wherein:
$R_5$ is $C_3$-$C_7$ secondary alkyl or monochloralkyl $C_3$-$C_4$;
X is $CH_3$, —$CH_2$—O—$CH_3$ or —$CH(CH_3)$—O—$CH_3$; and
$R_7$ is $CH_3$, $C_2H_5$, $C_3H_7$—n, $C_3H_7$—i, $C_4H_9$—i, $CF_3$ or Cl.

5. A process according to claim 4, wherein said aniline compound is n-sec. butyl-3, 4-xylidine N-(1-ethylpropyl)-3, 4-xylidine, or N-(1-methylbutyl)-3, 4-xylidine.

6. The process defined in claim 4 wherein the reaction mixture containing said dinitro derivative also contains spent nitric acid in a concentration of 10%-50% $HNO_3$ by weight, together with the subsequent step of repeating said process utilizing the said spent nitric acid in the said first-defined reacting step.

* * * * *

UNITED STATES PATENT AND TRADEMARK OFFICE
CERTIFICATE OF CORRECTION

PATENT NO. : 4,621,157
DATED : November 4, 1986
INVENTOR(S) : Larry A. McDaniel It is certified that error appears in the above-identified patent and that said Letters Patent is hereby corrected as shown below:

| | | |
|---|---|---|
| Col. 3, line 28 | HNO'hd 3 | $HNO_3$ |
| Col. 3, line 38 | "an aniline '38" | "an aniline" |
| Col. 3, line 66, | $C_2 14C_6$ | $C_2-C_6$ |
| Col. 12, line 8, | (1,83 moles) | (1.83 moles) |
| Col. 13, line 28, | 1:1.3 $HNO_3$ | 1:1.3 of $HNO_3$ |
| Col. 13, line 58 | $C_4H_9 13$ i, | $C_4H_9-i$, |
| Col. 13, line 60 | $-CH(CH_3)O-CH_3$ | $-CH(CH_3)-O-CH_3$ |
| Col. 13, lines 48-56 | 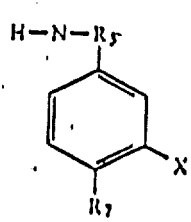 | 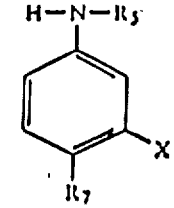 |

Signed and Sealed this

Fifth Day of September, 1989

*Attest:*

DONALD J. QUIGG

*Attesting Officer*     *Commissioner of Patents and Trademarks*